(12) United States Patent
Leong

(10) Patent No.: US 6,533,760 B2
(45) Date of Patent: Mar. 18, 2003

(54) FLASHBACK BLOOD COLLECTION NEEDLE

(75) Inventor: Alvin Tan Chee Leong, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/847,732

(22) Filed: May 2, 2001

(65) Prior Publication Data

US 2002/0004647 A1 Jan. 10, 2002

Related U.S. Application Data

(60) Provisional application No. 60/201,197, filed on May 2, 2000.

(51) Int. Cl.[7] ............................................. A61M 5/178
(52) U.S. Cl. ................... 604/168.07; 600/578
(58) Field of Search ....................... 604/168.07, 164.07, 604/93.01, 900; 600/578

(56) References Cited

U.S. PATENT DOCUMENTS

| | | | |
|---|---|---|---|
| 3,382,865 A | 5/1968 | Worrall ........................ 128/2 |
| 3,585,984 A | 6/1971 | Buchanan .................... 128/2 |
| 3,664,879 A | 5/1972 | Olsson | |
| 3,817,240 A | 6/1974 | Ayres | |
| 3,874,367 A | 4/1975 | Ayres | |
| 3,886,930 A | 6/1975 | Ryan | |
| 4,106,497 A | 8/1978 | Percarpio ..................... 128/2 |
| 4,108,175 A | 8/1978 | Orton .......................... 128/214 |
| 4,154,229 A | 5/1979 | Nugent ........................ 128/764 |
| 4,166,450 A | 9/1979 | Abramson ................... 128/764 |
| 4,193,400 A | 3/1980 | Loveless et al. ........... 128/214 |
| 4,207,870 A | 6/1980 | Eldridge | |
| 4,269,186 A | 5/1981 | Loveless et al. ........... 128/214 |
| 4,312,362 A | 1/1982 | Kaufman | |
| 4,317,445 A | 3/1982 | Robinson ................... 128/214 |

(List continued on next page.)

FOREIGN PATENT DOCUMENTS

| | | |
|---|---|---|
| EP | 0060385 | 9/1982 |
| EP | 0 139 872 A1 | 5/1985 |
| EP | 0 619 096 A1 | 10/1994 |
| JP | 58-183172 | 10/1983 |
| JP | 58-188460 | 11/1983 |
| JP | 58-212454 | 12/1983 |
| JP | 58212454 | 12/1983 |
| JP | 01223948 | 9/1989 |
| JP | 4132541 | 5/1992 |
| JP | 04364831 | 12/1992 |
| JP | 06007330 | 1/1994 |
| JP | 0713304 | 1/1995 |
| JP | 07039541 | 2/1995 |
| JP | 07039804 | 2/1995 |
| JP | 08150134 | 6/1996 |
| JP | 08257018 | 10/1996 |
| JP | 08275933 | 10/1996 |
| JP | 11028200 | 2/1999 |
| JP | 11169359 | 6/1999 |
| JP | 12139879 | 5/2000 |
| JP | 13000424 | 1/2001 |
| JP | 2001299729 | 2/2001 |
| JP | 12166903 | 3/2001 |
| JP | 13299728 | 10/2001 |
| WO | WO 99/03417 | 1/1999 |

*Primary Examiner*—Teresa Walberg
*Assistant Examiner*—Thor Campbell
(74) *Attorney, Agent, or Firm*—Nanette S. Thomas, Esq.; Scott J. Rittman, Esq.

(57) ABSTRACT

The needle assembly of the present invention includes a transparent or translucent housing having a fluid inlet end defined by a cylindrical exterior wall. The wall delineates an annular flashback chamber within the housing for retention of a fluid sample therein. The wall further includes a transparent or translucent construction or assimilation of a sealed window or port therein to allow immediate visualization of a fluid in the chamber.

12 Claims, 7 Drawing Sheets

U.S. PATENT DOCUMENTS

| | | |
|---|---|---|
| 4,340,068 A | 7/1982 | Kaufman |
| 4,398,544 A | 8/1983 | Nugent et al. |
| 4,409,990 A | 10/1983 | Mileikowsky ............... 128/763 |
| 4,412,548 A | 11/1983 | Hoch ......................... 128/764 |
| 4,416,290 A | 11/1983 | Lutkowski |
| 4,416,291 A | 11/1983 | Kaufman |
| 4,418,703 A | 12/1983 | Hoch et al. |
| 4,436,098 A | 3/1984 | Kaufman |
| 4,444,203 A | 4/1984 | Engelman |
| 4,679,571 A | 7/1987 | Frankel et al. |
| 4,788,986 A | 12/1988 | Harris ......................... 128/763 |
| 4,844,089 A | 7/1989 | Roberti ....................... 128/764 |
| 4,865,592 A | 9/1989 | Rycroft ....................... 604/197 |
| 4,886,072 A | 12/1989 | Percarpio et al. ........... 128/763 |
| 4,894,052 A | 1/1990 | Crawford ...................... 604/63 |
| 4,971,068 A | 11/1990 | Sahi ........................... 128/763 |
| 5,030,207 A | 7/1991 | Mersch et al. |
| 5,032,116 A | 7/1991 | Peterson et al. ............ 604/168 |
| 5,033,476 A | 7/1991 | Kasai .......................... 128/764 |
| 5,069,225 A | 12/1991 | Okamura ..................... 128/765 |
| 5,092,845 A | 3/1992 | Chang ......................... 604/164 |
| 5,112,327 A | 5/1992 | Iinuma et al. ............... 604/413 |
| 5,120,319 A | 6/1992 | Van Heugten et al. ...... 604/168 |
| 5,122,121 A | 6/1992 | Sos et al. .................... 604/167 |
| 5,137,518 A | 8/1992 | Mersch |
| 5,181,523 A | 1/1993 | Wendelborn ................ 128/764 |
| 5,201,794 A | 4/1993 | Kasai et al. ................... 73/863 |
| 5,217,025 A | 6/1993 | Okamura ..................... 128/765 |
| 5,222,502 A | 6/1993 | Kurose |
| 5,242,411 A | 9/1993 | Yamamoto et al. |
| 5,290,246 A | 3/1994 | Yamamoto et al. |
| 5,295,969 A | 3/1994 | Fischell et al. ............. 604/168 |
| 5,303,713 A | 4/1994 | Kurose |
| 5,306,259 A | 4/1994 | Fischell et al. ............. 604/239 |
| 5,450,856 A | 9/1995 | Norris |
| 5,496,281 A | 3/1996 | Krebs ......................... 604/168 |
| 5,520,193 A | 5/1996 | Suzuki et al. |
| 5,542,932 A | 8/1996 | Daugherty |
| 5,697,914 A | 12/1997 | Brimhall ..................... 604/177 |
| 5,755,701 A | 5/1998 | Sarstedt ....................... 604/264 |
| 5,830,190 A | 11/1998 | Howell ........................ 604/168 |
| 5,893,844 A | 4/1999 | Misawa ........................ 604/195 |
| 5,984,895 A | 11/1999 | Padilla et al. ............... 604/168 |
| 6,096,006 A | 8/2000 | Sarstedt et al. .............. 604/110 |
| 6,110,160 A | 8/2000 | Farber ......................... 604/412 |
| 6,156,010 A | 12/2000 | Kuracina et al. ............ 604/168 |
| 6,190,370 B1 | 2/2001 | Tsui ............................ 604/508 |
| 6,261,263 B1 | 7/2001 | Huet et al. ................... 604/168 |

FLASHBACK BLOOD COLLECTION NEEDLE

This application claims the benefit of Provisional application Ser. No. 60/201,197, filed May 2, 2000.

BACKGROUND OF THE INVENTION

1. Field of the Invention

The present invention relates to a device for collecting blood samples by performing venipuncture on a patient. More particularly, the present invention relates to a needle assembly for multiple sample blood collection that allows a phlebotomist to determine whether vein entry has occurred when collecting a blood sample from a patient into an evacuated blood collection tube.

2. Description of Related Art

Venipuncture is the primary method used for acquiring blood samples for laboratory testing. In performing venipuncture procedures, a phlebotomist must follow several steps simultaneously. Such steps include assessing the patient's overall physical and psychological condition so as to properly select a venipuncture site and technique. The phlebotomist must also select the proper corresponding equipment and perform the technique so as to not only control bleeding, but also to properly collect and identify fluid specimens for testing. The phlebotomist must ascertain all of these coinciding factors, as such factors may adversely affect the distension of the vein and the length of the venipuncture procedure.

Various venipuncture devices have been developed which address the above-described problems. These devices incorporate a needle assembly having a housing defining a chamber therewithin, wherein a single cannula pointed at both ends, is affixed to the housing. The intravenous end of the cannula is adapted for penetration of a patient's vein, and the non-patient end of the cannula has a sealable sleeve and adapted for penetration of a penetrable stop positioned within an evacuated container.

Upon vein entry with the intravenous end of the cannula, blood will flow through the cannula, into the sealable sleeve and into the housing chamber which is clear or translucent for visualization ("flashback"). Once air is vented from the housing chamber, the blood therewithin is pressurized each time the sealable sleeve is pushed toward the housing chamber upon activation of an evacuation container.

Due to the length of time between vein entry and flashback, the phlebotomist erroneously believes that satisfactory vein entry has not been achieved since there is no immediate indication thereof in the see-through chamber. Often the phlebotomist unnecessarily repeats the venipuncture procedure, requiring replacement of the evacuated container and/or the needle assembly itself. Such a repetitive process prolongs the physical and emotional discomfort endured by the patient.

It is therefore desirable to provide a fast, accurate and cost effective solution to conventional blood collection procedures upon which the phlebotomist may consistently rely on flashback to provide satisfactory venous entry. Moreover, it is particularly desirable to provide a blood collection device that permits blood flow through a relatively short needle directly into a flashback chamber, thereby providing immediate indication of successful vein entry.

SUMMARY OF THE INVENTION

The present invention provides a needle assembly for the extraction of at least one fluid sample into an evacuated container for laboratory testing, which needle assembly obviates the need for venting by providing a clear or translucent housing chamber with sufficient dead space for blood to flow into the chamber for visualization by the user to confirm successful vein entry.

A needle assembly is provided for collecting at least one fluid sample from a patient for subsequent discharge into at least one evacuated container. The needle assembly of the present invention includes a transparent or translucent housing having a fluid inlet end defined by a cylindrical exterior wall. The wall delineates an annular flashback chamber within the housing for retention of a blood sample therein. The housing further includes a fluid outlet end in communication with said fluid inlet end. A first cannula in fluid communication with the blood inlet end extends outwardly therefrom. The first cannula has an interior extremity positioned proximate the chamber and an exterior extremity opposed thereto that is adapted for puncture of a patient's vein. Similarly, a second cannula is provided in fluid communication with the fluid outlet end and extends outwardly therefrom. The second cannula has an interior extremity positioned proximate the first interior extremity and further includes an exterior extremity opposed to said second interior extremity. The second exterior extremity is adapted for puncture of a penetrable stopper in an evacuated container. The first and second cannulae are preferably in axial alignment with one another so as to provide an axial fluid flow path therebetween along a length of the housing. The second cannula further includes a sealable sleeve.

DETAILED DESCRIPTION

The present invention provides a needle assembly for blood collection that provides a visual indication of vein entry ("flashback") upon collection of a blood or other fluid sample from a patient into one or more evacuated blood collection tubes.

As illustrated in FIGS. 1–4, a needle assembly 10 of the present invention includes a transparent or translucent housing 12 which supports a fluid inlet needle (first cannula) on one side of the housing and a fluid outlet needle (second cannula) on an opposite side thereof. Fluid collected from the first cannula is immediately visualized through the housing to provide a timely indication of proper vein entry.

Figure 1:
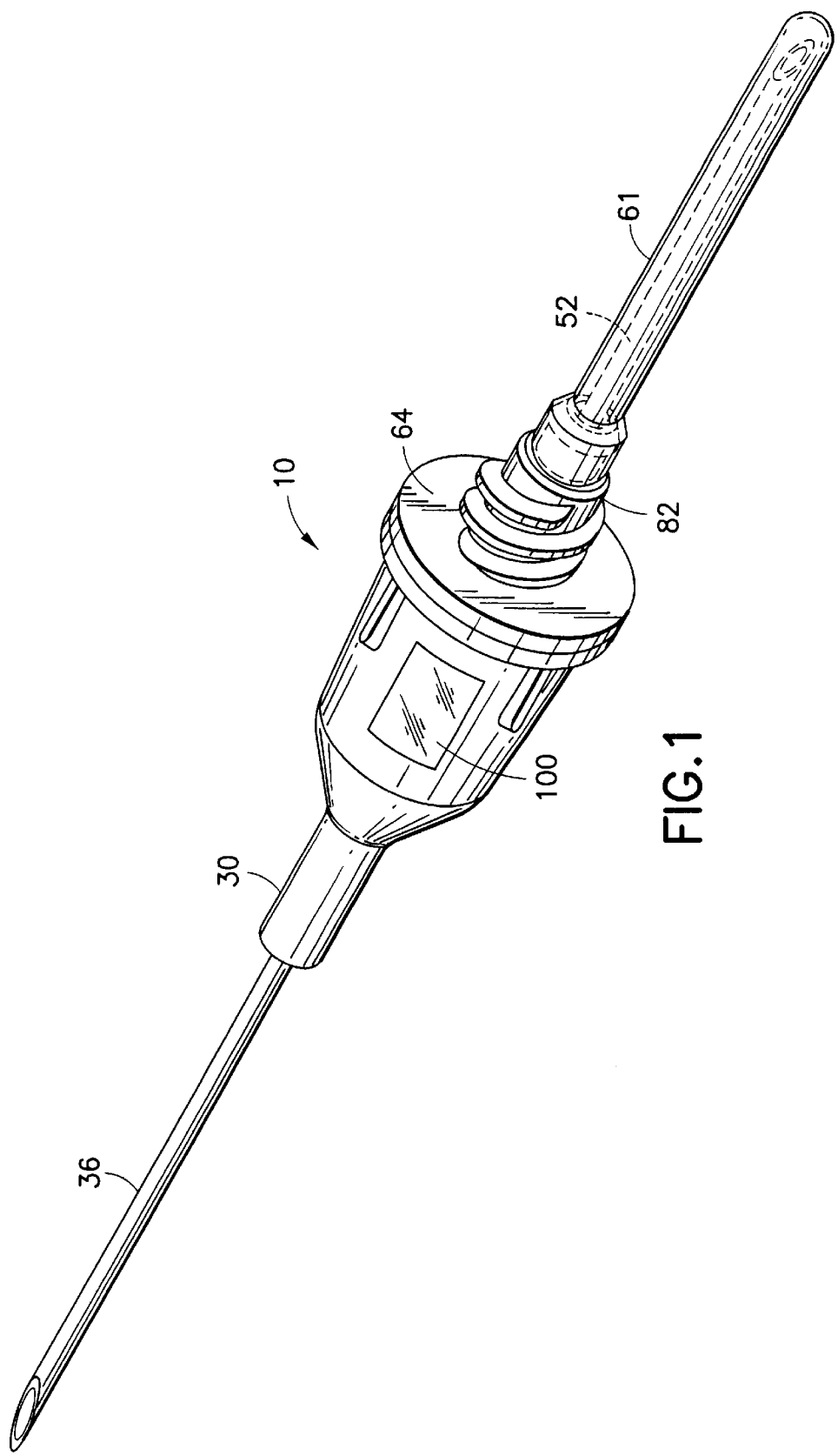
FIG. 1 is a perspective view of the needle assembly of the present invention.
Figure 2:
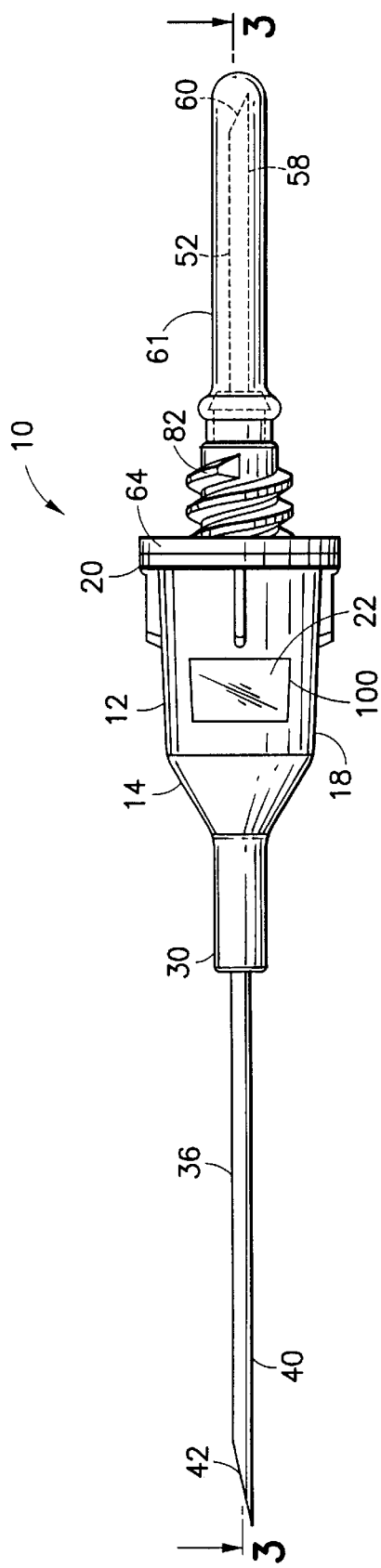
FIG. 2 is a side view of the needle assembly of FIG. 1.
Figure 3:
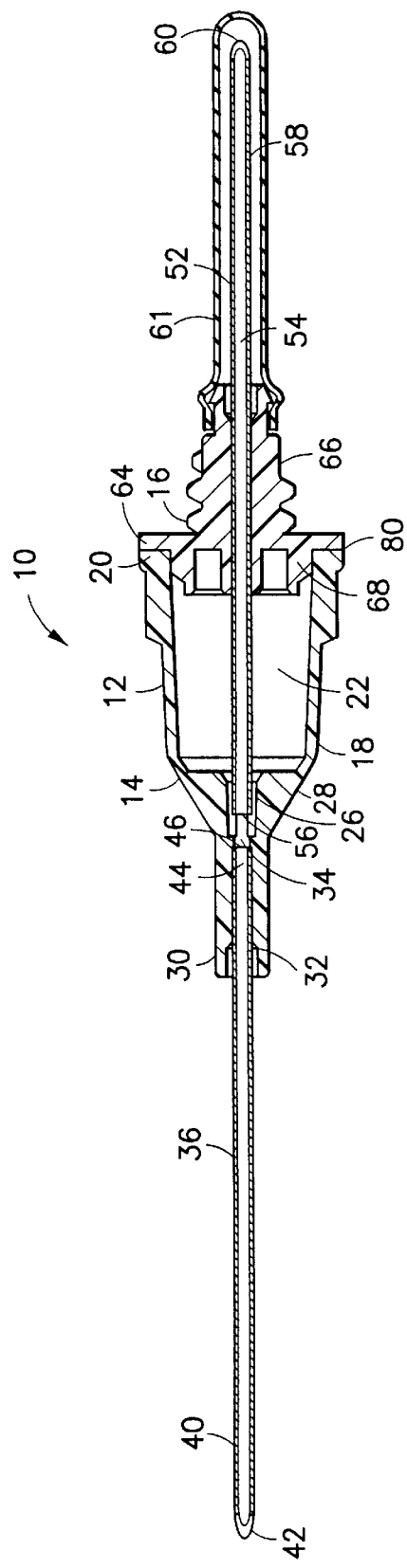
FIG. 3 is a side cross-sectional view of the needle assembly of FIG. 2 taken along 3—3 thereof.

As shown in FIGS. 1–3, needle assembly 10 includes a housing 12 having a fluid inlet end 14 and a fluid outlet end 16 adjacent thereto. Fluid inlet end 14 is defined by a cylindrical exterior wall 18 having an annular shoulder 20 protruding from an extremity thereof proximate fluid outlet end 16. Wall 18 circumscribes a flashback chamber 22 therein. Chamber 22 further includes an annular trench 26 defined within a frustoconical taper 28 depending outwardly from wall 18.

Fluid inlet end 14 is further defined by an injection end 30 wherein a cylindrical extension 32 is provided. Cylindrical extension 32, having an outer diameter smaller than an inner diameter of wall 18, protrudes outwardly from wall 18 with frustoconical taper 28 providing a bridge therebetween.

Cylindrical extension 32 has a large bore 34 extending therethrough which is sized to accommodate insertion and securement of a first fluid inlet cannula 36 therein. First cannula 36 has an exterior extremity 40 projecting outwardly from injection end 30 and further has a sharpened bevel 42. A first interior extremity 44 is defined at an opposite end of cannula 36 having a blunt tip 46 for insertion of cannula 36 in injection end 30. Bevel 42 and blunt tip 46 each include a correspondingly configured opening for uninterrupted passage of a fluid therethrough.

First cannula 36 is positioned in bore 34 such that first interior extremity 44 lies proximate annular trench 26 so as to remain in fluid communication therewith. Once cannula 36 is properly positioned, it may be frictionally engaged by bore 34 or affixed therein by means of an adhesive or the like.

Bore 34 spans an extent of cylindrical extension 32 and extends into taper 28 so as to be in communication with each of first cannula 36 and a second fluid outlet cannula 52. Second cannula 52, has a second interior extremity 54 with a blunt tip 56. Blunt tip 56 circumscribes the opening within trench 26 so as to be adjacent first interior extremity 44 of first cannula 36. Second cannula 52 further includes an exterior extremity 58 having a non-patient bevel end 60. Second cannula 52 extends outwardly from fluid outlet end 16 so as to form an elongate fluid passageway through housing 12. Non-patient bevel end 60 further includes a sealable sleeve 61 covering exterior extremity 58.

Fluid outlet end 16 of housing 12 includes a disc-like base 64 having a cylindrical protrusion 66 extending outwardly therefrom. Base 64 includes an annular flange 68 which is seated in cooperation with annular shoulder 20 of fluid inlet end 14 so as to form an interface 80 therebetween. The ends may be secured together along interface 80 by appropriate fastening means such as adhesives or the like.

Figure 4:
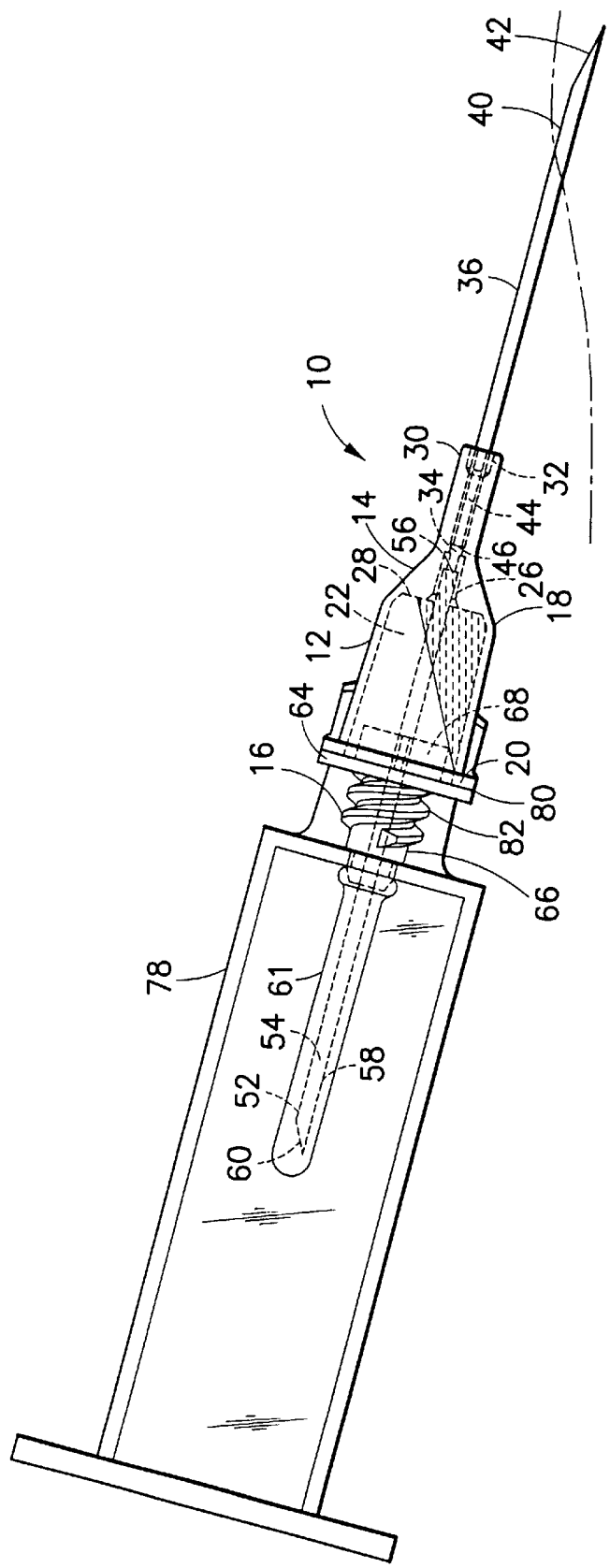
FIG. 4 illustrates the use of the needle assembly of FIG. 1 with a conventional needle holder.

As shown in FIG. 4, fluid outlet end 16 preferably includes means for securing needle assembly 10 to a holder 78 thereto. Such means includes a plurality of helical threads 82. Although a system of mating threads is shown herein, it is understood that any attachment means conducive to the practice of the present invention may be utilized.

Housing 12 is constructed from a translucent or transparent material so that a user of the assembly can readily view the contents of chamber 22. Although translucent rigid plastic is desirable, various sealed ports or windows such as window 100 shown in FIG. 2 may be used which enable the user to view the contents within chamber 22.

As shown in FIG. 4, during a conventional venipuncture procedure, needle assembly 10 as connected to holder 78 punctures the patient's skin to make a vein entry. Flashback chamber 22 provides sufficient space in chamber 22 to allow blood to flow beyond the opening of interior extremity 44 into trench 26 for instantaneous flashback visualization in relation to venous entry. In this manner, the phlebotomist has an almost instant visual indication that vein entry has been satisfactorily achieved by first cannula 36. Thus, upon satisfactory vein entry, air that is at atmospheric pressure within chamber 22 experiences compression due to the influence of venous pressure. Because the venous pressure exceeds the atmospheric pressure within chamber 22, blood flows thereinto and covers the opening of second interior extremity 54. Blood flow ceases once the pressure within chamber 22 and the venous pressure are equal.

Figure 5:
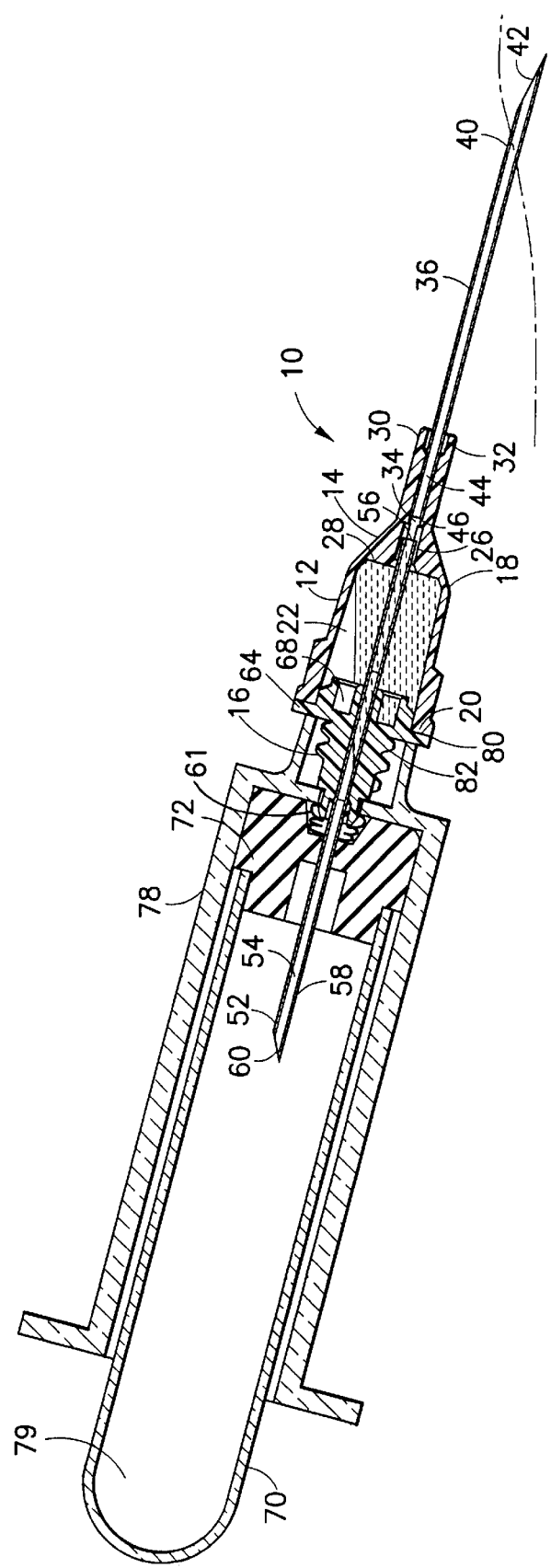
FIG. 5 is a cross-sectional view of the needle assembly in use with a conventional needle holder and a container during venipuncture of a patient's arm.

Once venous entry is visually confirmed by the phlebotomist, container 70, which is evacuated, is then inserted into holder 78 such that bevel 60 of second cannula 52 penetrates stopper 72 as shown in FIG. 5. Upon entrance into a vacuum portion 79 by second cannula 52, a negative pressure gradient is transmitted to the needle assembly. A lower pressure within the container causes blood to flow from the vein and into the container. Because axially aligned cannulae 36 and 52 provide an unblocked path for blood flow into container 70, under the influence of the negative pressure gradient. The blood present in trench 26 and chamber 22 is drawn into container 70 through the opening of second interior extremity 54 because of the negative pressure gradient in chamber 22. When this occurs, the pressure within chamber 22 and trench 26 drops below the patient's venous pressure, whereby the higher venous pressure will pressurize trench 26 and chamber 26 back to venous pressure again. The net effect is that a small column of blood, pulsating within trench 26, attempts to close the opening and minimizing air within chamber 22 from being drawn into container 70 by second interior extremity 54. Blood may be collected into multiple evacuated containers so that corresponding multiple samples may be obtained using a single needle assembly 10. The venipuncture procedure is terminated by removal of first cannula 36 from the patient's vein.

Figure 6:
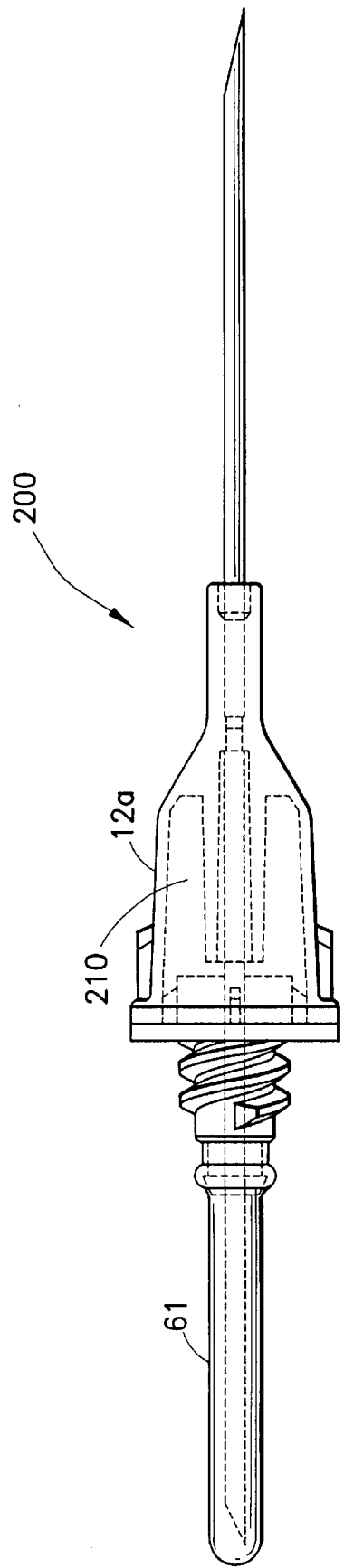
FIG. 6 is a cross-sectional view of an alternate embodiment of the needle assembly of the present invention.
Figure 7:
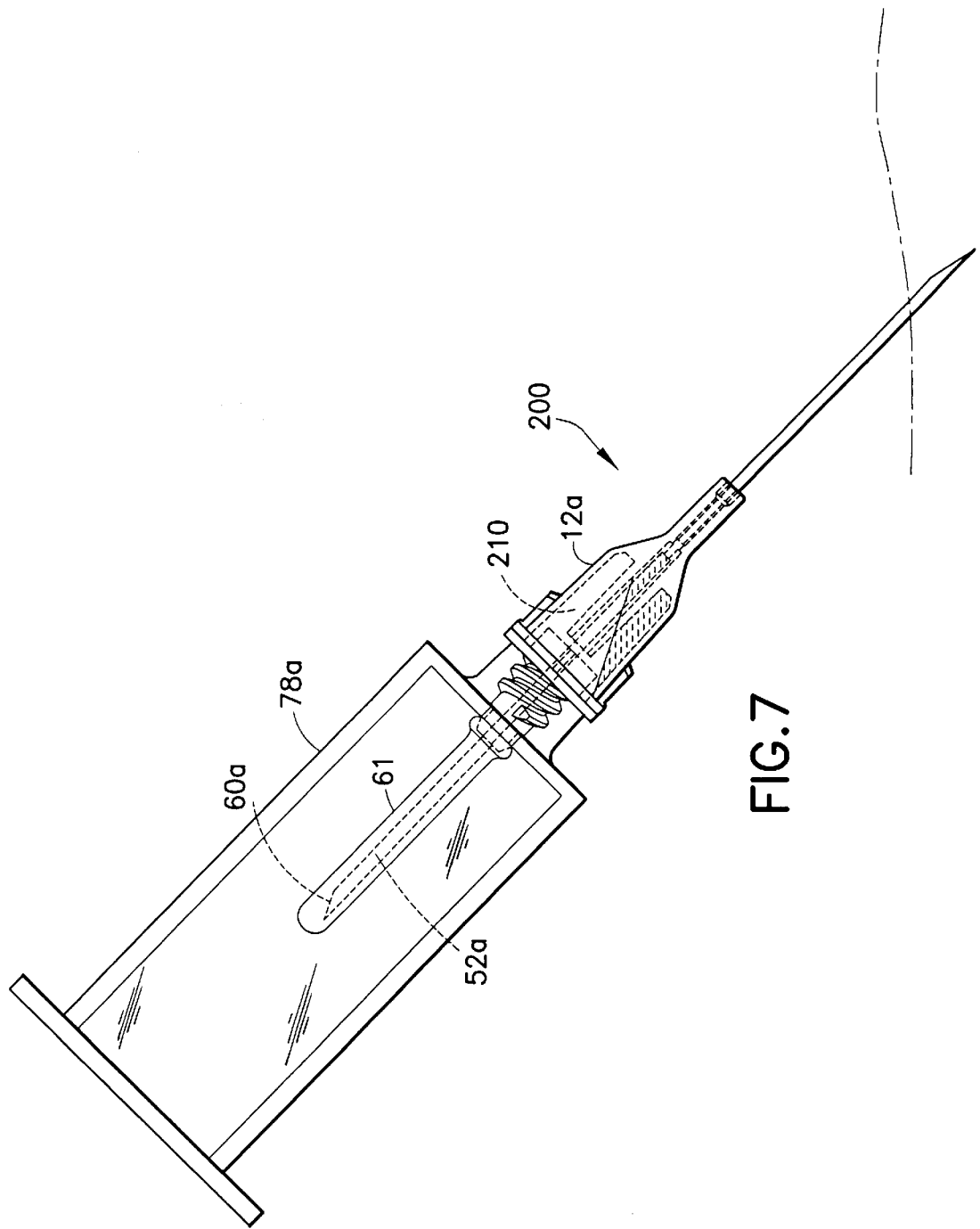
FIG. 7 illustrates the use of the needle assembly of FIG. 6 with a conventional needle holder.
Figure 8:
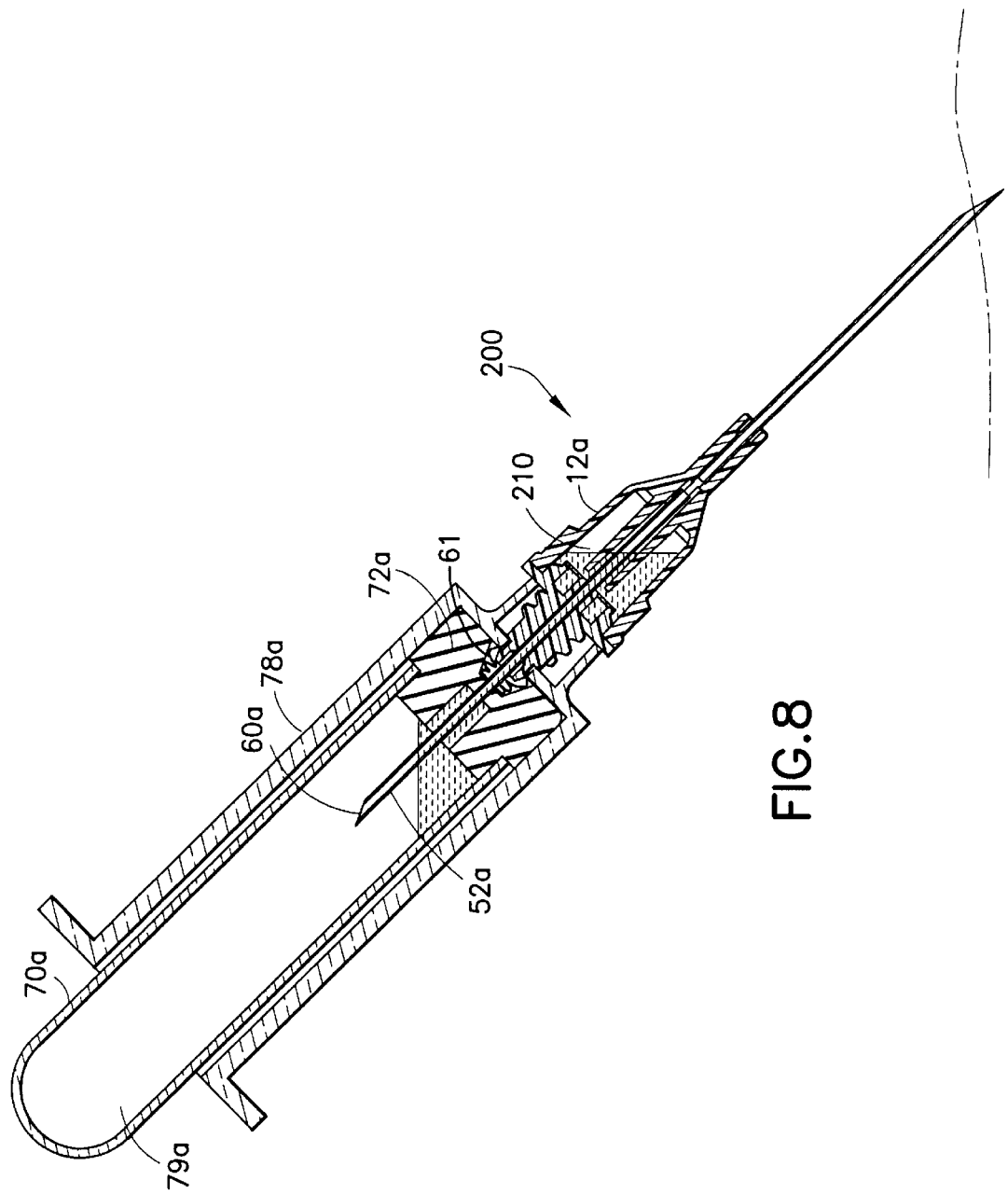
FIG. 8 is a cross-sectional view of the needle assembly in use with a conventional needle holder and a container during venipuncture of a patient's arm.

An additional embodiment of the present invention, as shown in FIGS. 6–8 includes many components which are substantially identical to the components of FIGS. 1–5. Accordingly, similar components performing similar functions will be numbered identically to those components of FIGS. 1–5, except that a suffix "a" will be used to identify those similar components of FIGS. 6–8.

FIG. 6 shows an alternate embodiment of the present invention, needle assembly 200 comprising an elongated flashback chamber 210 defined within housing 12a. Chamber 210 includes an elongated area for retention of a fluid sample therewithin. Chamber 210 includes a substantially concave curvature that provides enhanced visual magnification during sample collection.

As illustrated in FIG. 7 during a conventional venipuncture, needle assembly 200 as connected to holder 78a, punctures the patient's skin to make a vein entry. Chamber 210 indicates successful vein entry and reduces the draw of air present in housing 12a. Thus, upon satisfactory vein entry, air that is at atmospheric pressure within chamber 210 experiences compression due to the influence of venous pressure. Because the venous pressure exceeds the atmospheric pressure within chamber 210, blood flows thereinto. Blood flow ceases once the pressure within chamber 210 and the venous pressure are equal.

Once venous entry is visually confirmed by the phlebotomist, container 70a, which is evacuated, is then inserted into holder 78a such that bevel 60a of second cannula 52a penetrates stopper 72a as shown in FIG. 8. Upon entrance into vacuum portion 79a by second cannula 52a, a negative pressure gradient is transmitted to chamber

210. A lower pressure within the container causes blood to flow from chamber 210 into the container.

Various other changes and modifications may be effected therein by one skilled in the art without departing from the scope or spirit of the invention, and it is intended to claim all such changes and modifications as fall within the scope of the invention.

What is claimed is:

1. A needle assembly comprising:
    a housing having a fluid inlet end and an opposed fluid outlet end in communication therewith, the housing comprising an annular chamber and an annular trench adjacent to and in fluid communication with the chamber, the chamber and the trench providing for external visualization of a fluid present therein;
    a first cannula in fluid communication with said fluid inlet end and extending outwardly therefrom, said first cannula having a first interior extremity with an opening positioned proximate said trench and a first exterior extremity opposite thereto; and
    a second cannula in fluid communication with said fluid outlet end and extending outwardly therefrom, said second cannula having a second interior extremity with an opening positioned proximate said first interior extremity, said second cannula further having a second exterior extremity opposed to said second interior extremity, wherein a portion of the outside surface of the second cannula delineates the inner wall of the annular trench.

2. The needle assembly of claim 1, wherein the first and second cannulae are in axial alignment with each other, such that an axial flow path therebetween exists along a portion of the housing.

3. The needle assembly of claim 1, wherein an end of the first interior extremity is in fluid communication with the annular trench and the opening of the second interior extremity.

4. The needle assembly of claim 1, wherein the housing is free of air vents.

5. The needle assembly of claim 1, wherein an exterior wall of the housing is formed from a transparent or translucent plastic.

6. The needle assembly of claim 1, wherein an exterior wall of the housing comprises a transparent or translucent window region.

7. A needle assembly comprising:
    a housing having a first end and a second opposed end in fluid communication therewith, the housing comprising an annular chamber and an annular trench adjacent to and in fluid communication with the chamber, the chamber and the trench providing for external visualization of a fluid present therein;
    a first cannula in fluid communication with the first end and extending outwardly therefrom, the first cannula having a first interior extremity with an opening positioned proximate the trench and a first exterior extremity opposite thereto; and
    a second cannula in fluid communication with the second end and extending outwardly therefrom, the second cannula having a second interior extremity and a second exterior extremity opposed to the second interior extremity, wherein the second interior extremity comprises an opening proximate the first interior extremity, and wherein a portion of the outside surface of the second cannula delineates the inner wall of the annular trench.

8. The needle assembly of claim 7, wherein the first and second cannulae are in axial alignment with each other, such that an axial flow path therebetween exists along a portion of the housing.

9. The needle assembly of claim 7, wherein an end of the first interior extremity is in fluid communication with the annular trench and the opening of the second interior extremity.

10. The needle assembly of claim 7, wherein the housing is free of air vents.

11. The needle assembly of claim 7, wherein an exterior wall of the housing is formed from a transparent or translucent plastic.

12. The needle assembly of claim 7, wherein an exterior wall of the housing comprises a transparent or translucent window region.

* * * * *